US007869870B1

(12) United States Patent  
Farazi

(10) Patent No.: US 7,869,870 B1  
(45) Date of Patent: Jan. 11, 2011

(54) SYSTEM AND METHOD OF USING VAGAL STIMULATION TO ASSESS AUTONOMIC TONE AND RISK OF SUDDEN CARDIAC DEATH IN AN IMPLANTABLE CARDIAC DEVICE

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1656 days.

(21) Appl. No.: 10/861,747

(22) Filed: Jun. 4, 2004

(51) Int. Cl.
*A61N 1/362* (2006.01)

(52) U.S. Cl. .......................................... 607/9

(58) Field of Classification Search ............ 607/2, 607/9, 118, 119; 600/521
See application file for complete search history.

(56) References Cited

U.S. PATENT DOCUMENTS

| 5,330,507 | A  | * | 7/1994  | Schwartz    | 607/14  |
|-----------|----|---|---------|-------------|---------|
| 6,922,585 | B2 | * | 7/2005  | Zhou et al. | 600/518 |
| 7,079,887 | B2 | * | 7/2006  | Burnes et al.| 600/510|
| 7,225,017 | B1 | * | 5/2007  | Shelchuk    | 607/4   |
| 2003/0191403 | A1 | | 10/2003 | Zhou et al. | 600/515 |

FOREIGN PATENT DOCUMENTS

WO    WO 03/086187 A1    10/2003

OTHER PUBLICATIONS

Schmidt G et al., Heart-rate turbulence after ventricular premature beats as a predictor of mortality after acute myocardial infarction, The Lancet, Apr. 24, 1999, vol. 353, 1390-1396.*
Malik, et al., "Heart-rate Turbulence", G Ital Cardiol, vol. 29, Suppl 5, 1999, 5 pages.
Mrowka, et al., "Blunted Arterial Baroreflex Causes "Pathological" Heart Rate Turbulence", Am J Physiol Regulatory Integrative Comp Physiol 279: R117-R1175, 2000.
Schmidt, et al., "Heart-rate Turbulence After Ventricular Premature Beats as a Predictor of Mortality After Acute Myocardial Infarction", The Lancet, vol. 353, Apr. 24, 1999, pp. 1390-1396.

(Continued)

*Primary Examiner*—Carl H Layno
*Assistant Examiner*—Brian T Gedeon
(74) *Attorney, Agent, or Firm*—Steven M. Mitchell

(57) ABSTRACT

A method and apparatus for using vagal stimulation to detect autonomic tone and assess a patient's risk of sudden cardiac death (SCD) are presented. The method involves stimulating the patient's vagus nerve in order to induce a drop in arterial blood pressure, which simulates the patient's cardiovascular response to a premature ventricular contraction (PVC). Sinus rhythm data just before and immediately following the stimulation is recorded and analyzed for a degree of heart rate turbulence (HRT) in order to detect abnormalities in autonomic tone and assess the risk of SCD. In an embodiment, the method is implemented in an implantable cardiac device (ICD), which can deliver arrhythmia prevention therapy based on the risk of SCD. The method can assess the patient's vagal activity on-demand by measuring HRT without relying on naturally occurring PVCs and eliminates the risk of causing arrhythmia associated with artificially inducing PVCs in order to measure HRT.

39 Claims, 6 Drawing Sheets

OTHER PUBLICATIONS

Berkowitsch, et al., "Prognostic Significance of Heart-rate Turbulence in ICD Patients with DCM", The XIIth World Congress on Cardiac Pacing & Electrophysiology, Hong Kong, Feb. 19-22, 2003, pp. 299-303.

Cygankiewicz, et al., "Heart Rate Turbulence Predicts Cardiac Death in Patients Undergoing CABG Surgery", Abstract ID: 102431, Publishing ID: 396, 1 page.

Bauer, et al., "Dynamics of Heart Rate Turbulence Predicts Mortality After Acute Myocardial Infarction", 1 page.

Wichterle, et al., "Turbulence Slope after Atrial Premature Complexes is Significant Mortality Predictor in Patients after Myocardial Infarction", Abstract: 814-4, Citation: Supplement to Journal of the American College of Cardiology, Mar. 19, 2003, vol. 41, Issue 6, Suppl. A, 2 pages.

Lindgren, et al., "Heart Rate Turbulence after Ventricular and Atrial Premature Beats in Subjects without Structural Heart Disease", Abstract, Journal of Cardiovascular Electrophysiology, vol. 14, Issue 5, p. 447, May 2003.

"Heart Rate Turbulence Calculation", Technische Universitat Munchen, 2 pages.

"Heart Rate Turbulence HRT!View" Technische Universitat Munchen, 2 pages.

Jeron, et al., "Association of the Heart Rate Turbulence with Classic Risk Stratification Parameters in Postmyocardial Infarction Patients", A.N.E., Oct. 2003, vol. 8, No. 4, pp. 296-301.

Davies, et al., "Relation of Heart Rate and Blood Pressure Turbulence Following Premature Ventricular Complexes to Baroreflex Sensitivity in Chronic Congestive Heart Failure", The American Journal of Cardiology, vol. 87, Mar. 15, 2001, pp. 737-742.

Lin, et al., "Tight Mechanism Correlation Between Heart Rate Turbulence and Baroreflex Sensitivity: Sequential Autonomic Blockage Analysis", Journal of Cardiovascular Electrophysiology, vol. 13, No. 5, May 2002, pp. 427-431.

Wichterle, et al., "Mechanisms Involved in Heart Rate Turbulence", Cardiac Electrophysiology Review 2002, vol. 6, No. 3, pp. 262-266.

Watanabe, et al., "Effects of Ventricular Premature Stimulus Coupling Interval on Blood Pressure and Heart Rate Turbulence", Circulation, Jul. 16, 2002, pp. 325-330.

* cited by examiner

LOW-RISK OF SCD

HIGH-RISK OF SCD

SYSTEM AND METHOD OF USING VAGAL STIMULATION TO ASSESS AUTONOMIC TONE AND RISK OF SUDDEN CARDIAC DEATH IN AN IMPLANTABLE CARDIAC DEVICE

BACKGROUND OF THE INVENTION

1. Field of the Invention

The present invention relates generally to implantable cardiac devices and, more particularly, to systems and methods for assessing autonomic tone and a patient's risk of sudden cardiac death (SCD).

2. Background Art

A ventricular premature beat (VPB) triggers fluctuation in cardiac cycle duration and a brief disturbance to arterial blood pressure, referred to as heart rate turbulence (HRT) by Schmidt et al., "Heart-rate turbulence after ventricular premature beats as a predictor of mortality after acute myocardial infarction," Lancet 353:1390-96 (1999). Schmidt et al. define HRT as a characteristic initial acceleration and subsequent deceleration of sinus rhythm after a single VPB. The study by Schmidt et al. shows that the degree of HRT following a VPB can predict a patient's risk of SCD; for example, HRT is absent in the sinus rhythm of a high-risk patient but is present in the sinus rhythm of a low-risk patient. Schmidt et al. also defined two parameters to quantify the degree of HRT following a VPB: HRT onset, which is the initial acceleration of sinus rhythm after a single VPB, and HRT slope, which is the speed of the subsequent deceleration of sinus rhythm after a single VPB.

The degree of HRT following a VPB can also detect autonomic abnormalities. For example, U.S. Patent Application Publication No. 2003/0191403 A1, entitled "Method and apparatus for predicting recurring ventricular arrhythmias," to Zhou et al., explains that changes in the autonomic nervous system are known contributing factors to arrhythmia development. Zhou et al. further explain that heart rate is regulated by the sympathetic and parasympathetic components of the autonomic nervous system, and that increased sympathetic activity (i.e., sympathetic tone) causes the heart rate to increase, while increased parasympathetic activity (i.e., vagal tone) causes the heart rate to decrease. Accordingly, Zhou et al. propose that monitoring changes in autonomic tone might be useful for predicting arrhythmia development.

A study by Lin et al., "Tight mechanism correlation between heart rate turbulence and baroreflex sensitivity: sequential autonomic blockade analysis," Journal of Cardiovascular Electrophysiology, 13:427-431 (May 2002), demonstrated that because HRT is abolished when the vagus nerve is blocked, maintenance of normal HRT following a VPB is dependent on vagal tone. Lin et al. also showed that the parameters HRT onset and HRT slope are vagally dependent and, accordingly, can be used as indirect measures of vagal tone.

Additionally, Lin et al. showed that the parameters HRT onset and HRT slope are highly correlated with spontaneous baroreflex, which is described by Lin et al. as the negative feedback system that modulates dynamic fluctuations of heart rate and arterial blood pressure. A study by Mrowka et al., "Blunted arterial baroreflex causes 'pathological' heart rate turbulence," Am J Physiol Regulatory Integrative Comp Physiol, 279:R1171-75 (2000), explained that a VPB followed by a compensatory pause leads to a drop in arterial blood pressure; therefore, baroreflex action is essential for compensating blood pressure. Wichterle et al., "Mechanisms involved in heart rate turbulence," Cardiac Electrophysiology Review, 6:262-266 (2002) propose that the compensatory pause following a VPB triggers HRT as a response to the sudden decrease in arterial blood pressure.

One approach for assessing autonomic tone and a patient's risk of SCD is to measure the degree of HRT after a naturally occurring (i.e., intrinsic) premature ventricular contraction (PVC) caused by a VPB. A disadvantage of this technique, however, is it cannot be executed on-demand or at regular intervals. Another approach for assessing autonomic tone and a patient's risk of SCD, when naturally occurring PVCs are absent, is to measure the degree of HRT following an artificially induced PVC. A disadvantage of this technique, however, is that artificially inducing PVCs in the absence of naturally occurring PVCs can cause arrhythmia.

What is needed, therefore, are a system and method for detecting abnormalities in autonomic tone and assessing a patient's risk of SCD by measuring a degree of HRT absent naturally occurring or artificially induced PVCs, i.e., on demand and without posing an arrhythmic risk.

BRIEF SUMMARY OF THE INVENTION

The present invention includes a system and method for detecting abnormalities in autonomic tone and assessing a patient's risk of SCD by measuring a degree of oscillatory behavior in sinus rhythm cycle immediately after the cardiovascular system is presented with a sudden drop in blood pressure similar to that seen immediately following a PVC. The method of the invention involves i stimulating the patient's vagus nerve in order to induce a drop in arterial blood pressure, which simulates the patient's cardiovascular response to a PVC. After stimulating the vagus nerve, sinus rhythm data is recorded. A degree of oscillatory behavior in the sinus rhythm data is measured in order to detect abnormalities in autonomic tone and assess the patient's risk of SCD.

In an embodiment, R-wave to R-wave sinus rhythm intervals ("RR intervals") just before and immediately following the premature event are recorded and a degree of HRT is measured. The degree of HRT is quantified by determining at least one of HRT onset, HRT slope, and HRT timing.

In another embodiment, the method is implemented in an implantable cardiac device (ICD). The ICD applies a stimulation burst to the patient's vagus nerve in order to induce a drop in arterial blood pressure. A quantity of RR intervals just before and immediately following the application of the stimulation burst are recorded and a degree of HRT is determined according to at least one of HRT onset, HRT slope, and HRT timing. After the ICD applies a desired number of stimulation bursts, abnormalities in autonomic tone can be detected and the patient's risk of SCD can be assessed. Additionally, the ICD can be configured to deliver appropriate arrhythmia prevention therapy to the patient based on detected autonomic abnormalities and the assessed risk.

The system of the invention includes means for stimulating the patient's vagus nerve in order to induce a drop in arterial blood pressure. The apparatus further includes means for monitoring the patient's sinus rhythm response following the stimulation. A processor measures a degree of oscillatory behavior in the recorded sinus rhythm response in order to detect abnormalities in autonomic tone and assess the patient's risk of SCD.

In an embodiment, stimulation of the patient's vagus nerve is performed by an ICD with a lead configured for applying stimulation bursts to the vagus nerve. The processor of the ICD measures a degree of HRT by determining at least one of HRT onset, HRT slope, and HRT timing. The ICD can also be configured to deliver appropriate arrhythmia prevention therapy to the patient based on detected autonomic abnormalities and the assessed risk.

The system and method of the present invention are advantageous, because vagal activity can be assessed on-demand by measuring HRT without relying on naturally occurring PVCs. The system and method also eliminate the risk of causing arrhythmia associated with artificially inducing PVCs in order to measure HRT. Additionally, by detecting patients who have a high risk of SCD, the system and method can trigger delivery of appropriate arrhythmia prevention therapies. The system and method are also advantageous for identifying pacemaker patients who have a high-risk of SCD, so that they can be outfitted with an ICD capable of delivering appropriate arrhythmia prevention therapies. Further features and advantages of the claimed embodiments of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Figure 1:
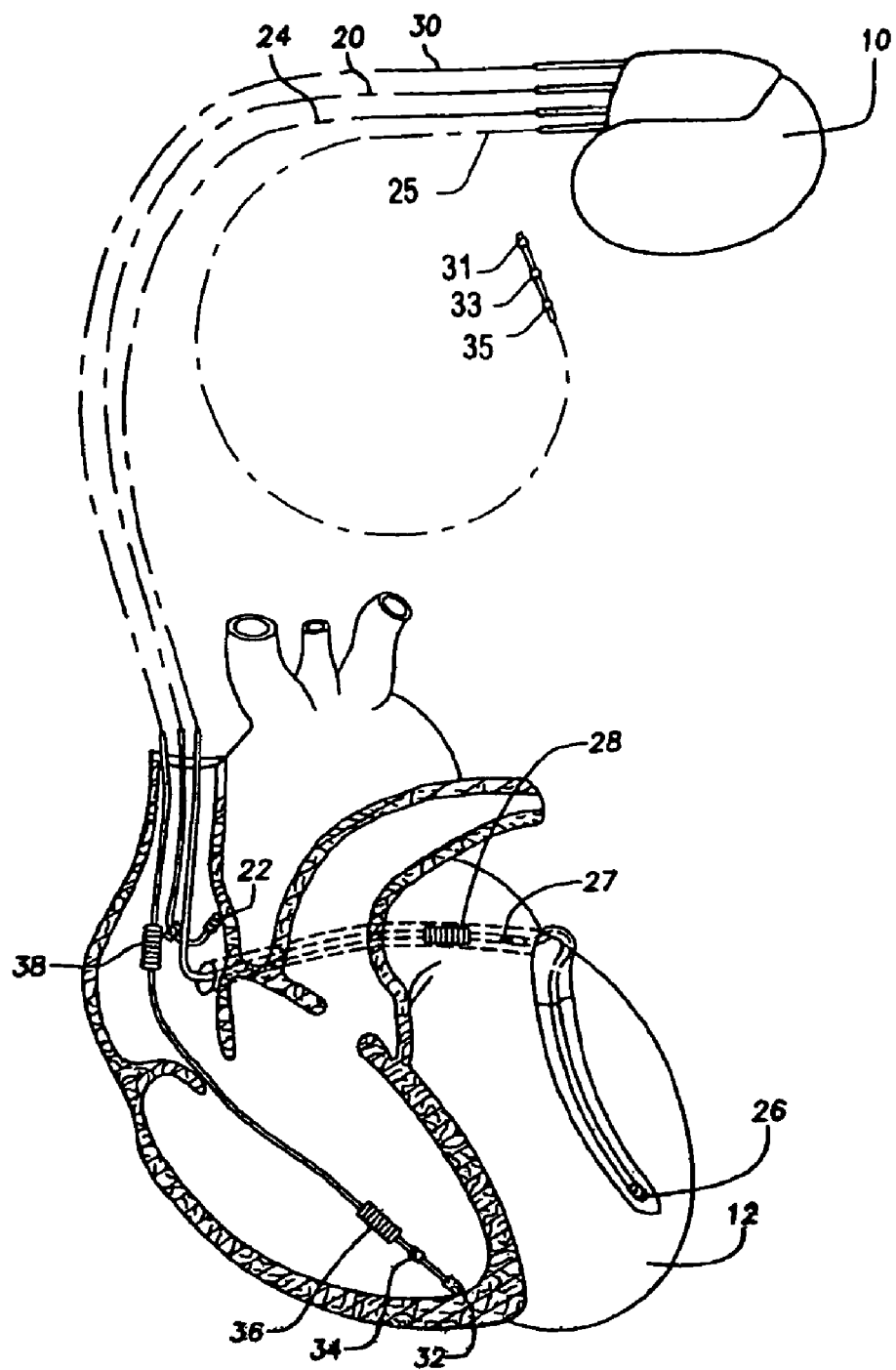
FIG. 1 is a simplified diagram illustrating an exemplary ICD in electrical communication with a patient's heart by means of three leads suitable for delivering multi-chamber stimulation and pacing therapy, and a fourth lead, in accordance with an embodiment of the present invention, suitable for delivering vagal stimulation.
Figure 2:
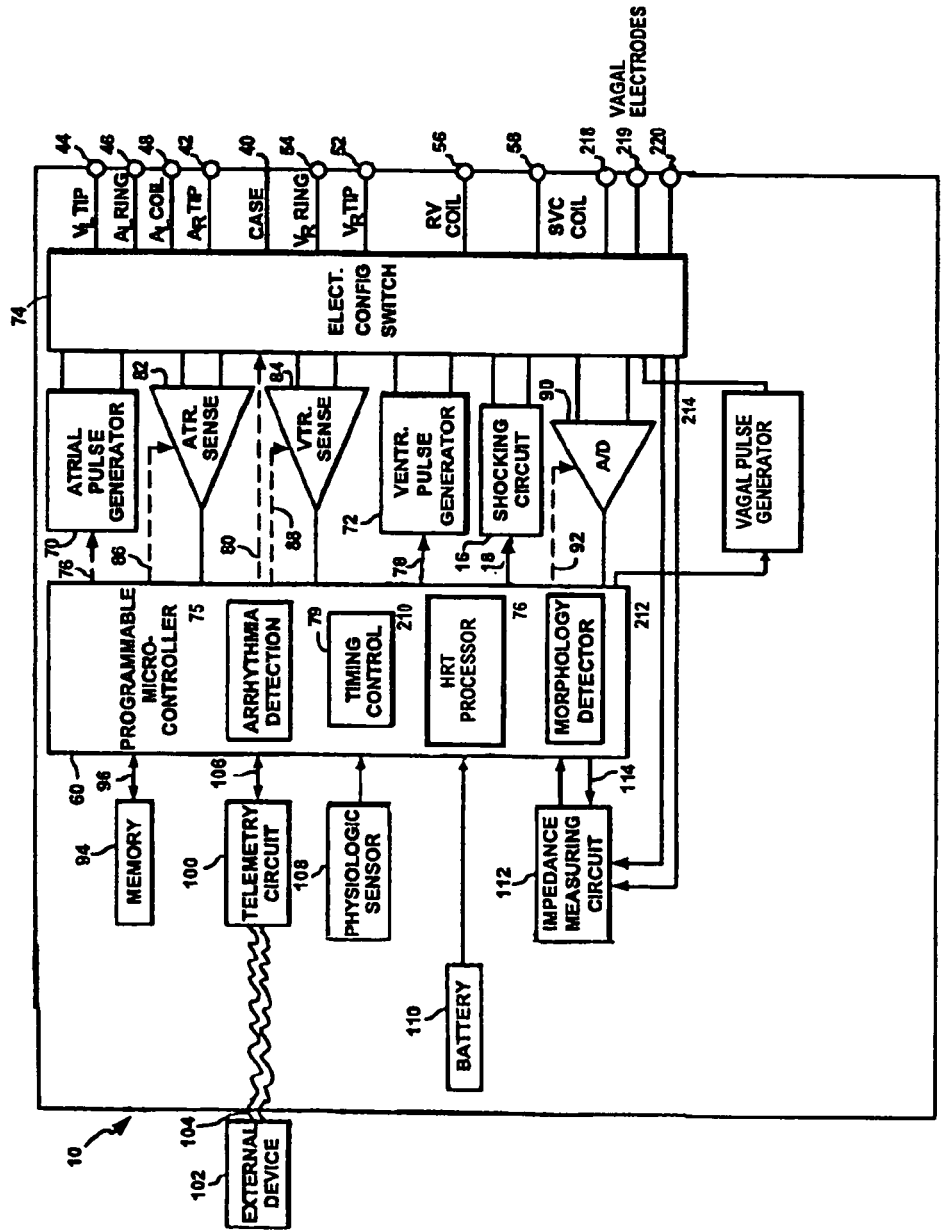
FIG. 2 is a functional block diagram of an exemplary ICD that can provide cardioversion, defibrillation, and pacing stimulation in four chambers of a heart, and assess a patient's risk of SCD, in accordance with an embodiment of the present invention.

Before describing the invention in detail, it is helpful to describe an example environment in which the invention may be implemented. The present invention is particularly useful in the environment of an ICD. An ICD is a medical device that is implanted in a patient to monitor electrical activity of a heart and to deliver appropriate electrical therapy, for example, pacing pulses, cardioverting and defibrillator pulses, and drug therapy, as required. ICDs include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment including the present invention.

Exemplary ICD in Electrical Communication with a Patient's Heart

FIG. 1 illustrates an exemplary ICD 10 is in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

As shown in FIG. 1, ICD 10 is also in electrical communication with the patient's heart 12 by way of a vagal stimulation lead 25, having three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

Functional Elements of an Exemplary ICD

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219, and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

In accordance with the present invention, the connector further includes vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Also shown in FIG. 2 is vagal pulse generator 214, in accordance with an embodiment of the present invention. Vagal pulse generator 214 is controlled by microcontroller 60 via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

In accordance with an embodiment of the present invention, microcontroller 60 includes an HRT processor 210, which controls the delivery of vagal stimulation pulses. HRT processor 210 triggers vagal pulse generator 214, via control signal 212, to deliver vagal stimulation pulses. HRT processor 210, in conjunction with arrhythmia detection circuitry 75, determines whether the patient is in normal sinus before triggering vagal pulse generator 214 to deliver vagal stimulation.

In an embodiment, HRT processor 210 triggers data acquisition circuit 90 and timing control circuit 79 to record RR intervals preceding and following delivery of a vagal stimulation pulse. HRT processor 210 measures a degree of oscillatory behavior in the recorded RR intervals in order to assess autonomic tone and the patient's risk of SCD. HRT processor 210 can also trigger ICD 10 to respond appropriately based on the assessed risk (e.g., by triggering vagal pulse generator 214 to deliver prolonged vagal stimulation, by triggering shocking circuit 16 to deliver high voltage shocks, and by triggering atrial pulse generator 70 and ventricular pulse generator 72 to deliver pacing pulses). Additionally, in conjunction with a telemetry circuit 100, HRT processor 210 can be configured to deliver status information, relating to the patient's assessed level of risk, to external device 102 through an established communication link 104.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

Advantageously, the operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 further includes a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Heart Rate Turbulence in Response to a Premature Ventricular Contraction

Figure 3:
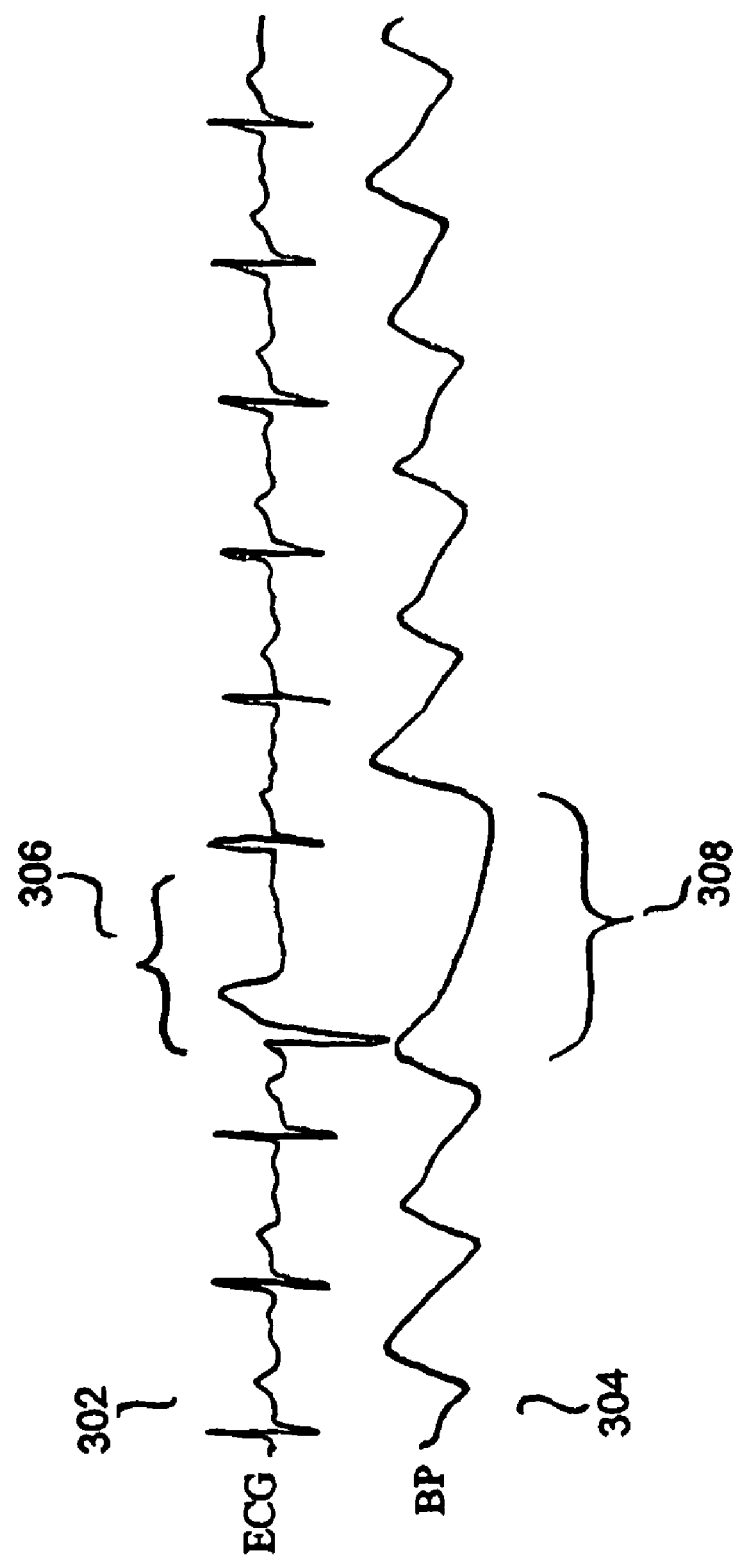
FIG. 3 illustrates an electrocardiogram (ECG) showing a PVC and a resulting disturbance in arterial blood pressure (BP).

A PVC triggered by a VPB causes a brief disturbance to arterial blood pressure. FIG. 3 illustrates an ECG trace 302 showing a PVC 306 and a resulting disturbance 308 in an arterial blood pressure trace 304. According to the present invention, arterial blood pressure disturbance 308 can also be triggered by stimulating the vagus nerve, which is advantageous because artificially inducing PVC 306 to trigger pressure disturbance 308 can cause arrhythmia.

Figure 4A:
FIG. 4A illustrates an ECG showing a PVC.
Figure 4B:
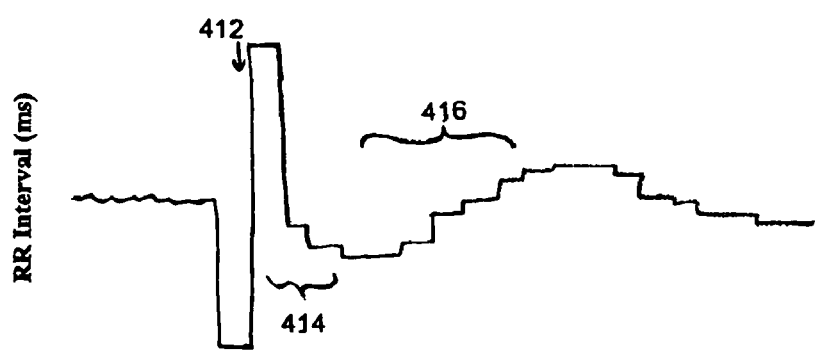
FIG. 4B illustrates the resulting fluctuation in sinus cycle length for a patient at low risk of SCD.
Figure 4C:
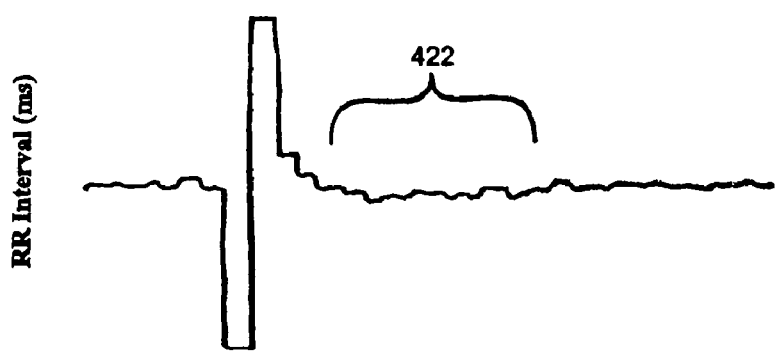
FIG. 4C illustrates the resulting fluctuation in sinus cycle length for a patient at high-risk of SCD.

FIG. 4A illustrates an ECG trace depicting a PVC 402. The resulting fluctuation in sinus cycle length, referred to as HRT, due to PVC 402 is shown in FIG. 4B for a patient at low risk of SCD and in FIG. 4C for a patient at high risk of SCD. The sinus rhythm of the high-risk patient, shown in FIG. 4C, contains negligible turbulence 422 in response to PVC 402, while the sinus rhythm of the low-risk patient, shown in FIG. 4B, contains a characteristic HRT pattern of an initial acceleration 414 and a subsequent deceleration 416 following PVC 402. According to the present invention, stimulating the patient's vagus nerve for a duration that simulates compensatory pause 412, shown in FIG. 4B, will trigger an intrinsic baroreflex response to a drop in blood pressure without causing an arrhythmia (i.e., stimulating the patient's heart tissue to trigger the intrinsic response might be arrhythmogenic). The intrinsic baroreflex response is observed in the form of HRT in low-risk patients, but is absent in high-risk patients due to impairment of baroreflex response activity.

Accordingly, a patient's risk of SCD can be assessed by monitoring a quantity of RR intervals preceding and following a PVC, and measuring the subsequent degree of HRT. For example, in FIG. 4B, HRT can be quantified by the parameters HRT onset and HRT slope. HRT onset quantifies the amount of initial acceleration 414, and HRT slope quantifies the speed of subsequent deceleration 416. Watanabe et al., "Effects of ventricular premature stimulus coupling interval on blood pressure and heart rate turbulence," Circulation, 106:325-330 (2002), describe another parameter, HRT timing, to quantify HRT. Watanabe et al. define HRT timing as the first beat number of a five-beat RR sequence having the maximum regression slope.

Thus, the degree of HRT can be determined by measuring an HRT parameter, such as HRT onset, HRT slope, or HRT timing, and comparing the measured value to a predefined threshold. For example, when the value of HRT onset is less than a threshold, or when the value of HRT slope is less than a threshold, a risk indicator can be triggered. The invention is not, however, limited to measuring HRT following a premature event. Based on the description herein, one skilled in the relevant art(s) will understand that the invention can be implemented by measuring other parameters that quantify the oscillatory behavior in RR intervals following a premature event and that also serve as surrogate measures of the level of vagal activity (e.g., mean magnitude of RR acceleration or deceleration, the overall morphology of the RR oscillation, time course of the overall oscillation, etc.).

Method of Assessing Autonomic Tone and Risk of Sudden Cardiac Death

Figure 5:
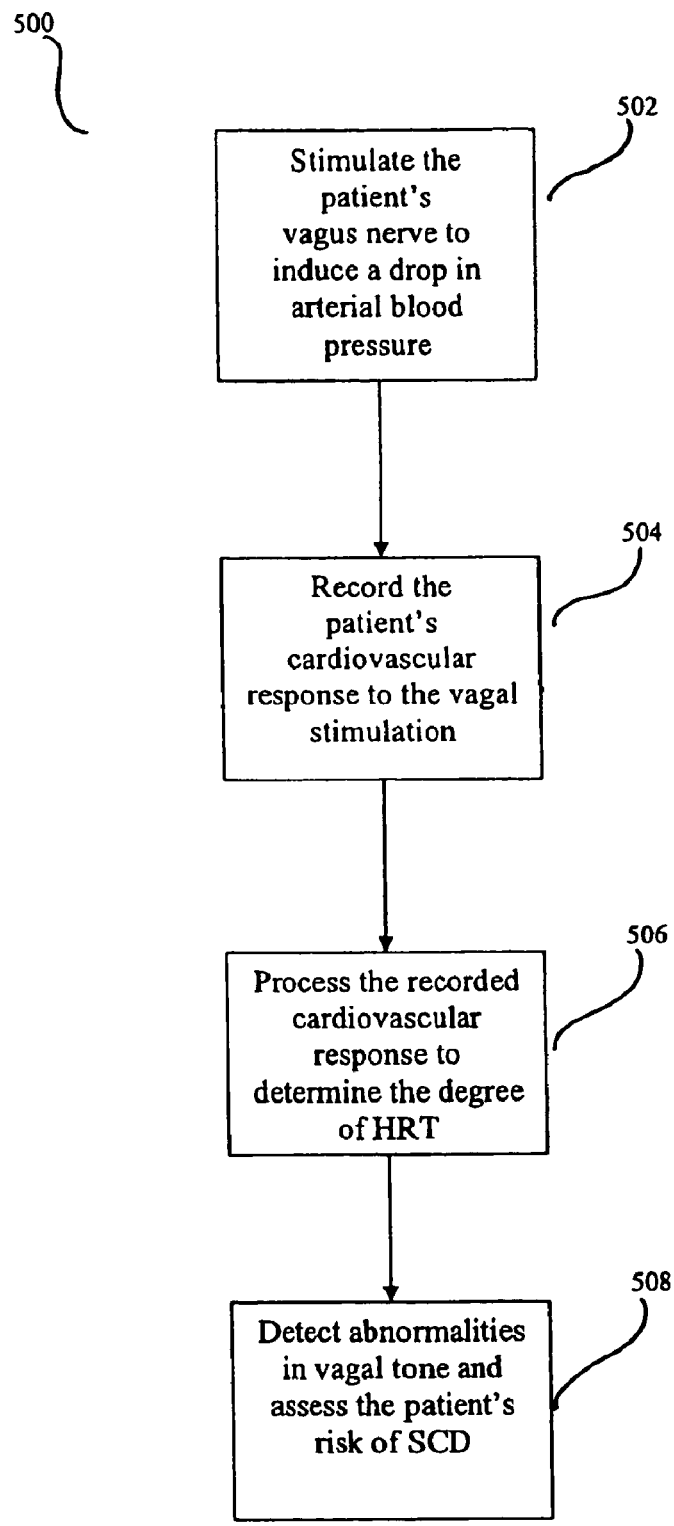
FIG. 5 is a high-level process flowchart, according to the present invention, illustrating a method for using vagal stimulation to assess autonomic tone and a patient's risk of SCD.

FIG. 5 is a high-level process flowchart, according to the present invention, illustrating a method 500 for using vagal stimulation to detect abnormalities in autonomic tone and assess a patient's risk of SCD. In step 502, the patient's vagus nerve is stimulated to induce a drop in arterial blood pressure. The blood pressure disturbance simulates the patient's response to a PVC. The patient's sinus rhythm response to the vagal stimulation and induced blood pressure disturbance is recorded in step 504. In step 506, the sinus rhythm data is processed in order to measure a degree of oscillatory behavior in the sinus rhythm intervals following the induced disturbance.

In step 508, the degree of oscillatory behavior measured in step 506 is analyzed in order to detect abnormalities in autonomic tone and assess the patient's risk of SCD. As described above, the degree of oscillatory behavior can be quantified by measuring a parameter indicative of HRT, such as HRT onset, HRT slope, and HRT timing, and comparing the measured parameter to a predefined threshold. For example, when the value of HRT onset is less than a threshold, or when the value of HRT slope is less than a threshold, a risk indicator can be triggered. In an embodiment, method 500 can be programmed to reevaluate the patient's response to vagal stimulation at predetermined intervals (e.g., weekly, monthly, etc.). Advantageously, method 500 can be performed on-demand because it does not depend on naturally occurring PVCs to induce a blood pressure disturbance and trigger oscillatory behavior in subsequent sinus rhythm intervals. Also, method 500 eliminates the risk of causing arrhythmia associated with artificially inducing PVCs to induce a blood pressure disturbance and trigger oscillatory behavior in subsequent sinus rhythm intervals.

Figure 6:
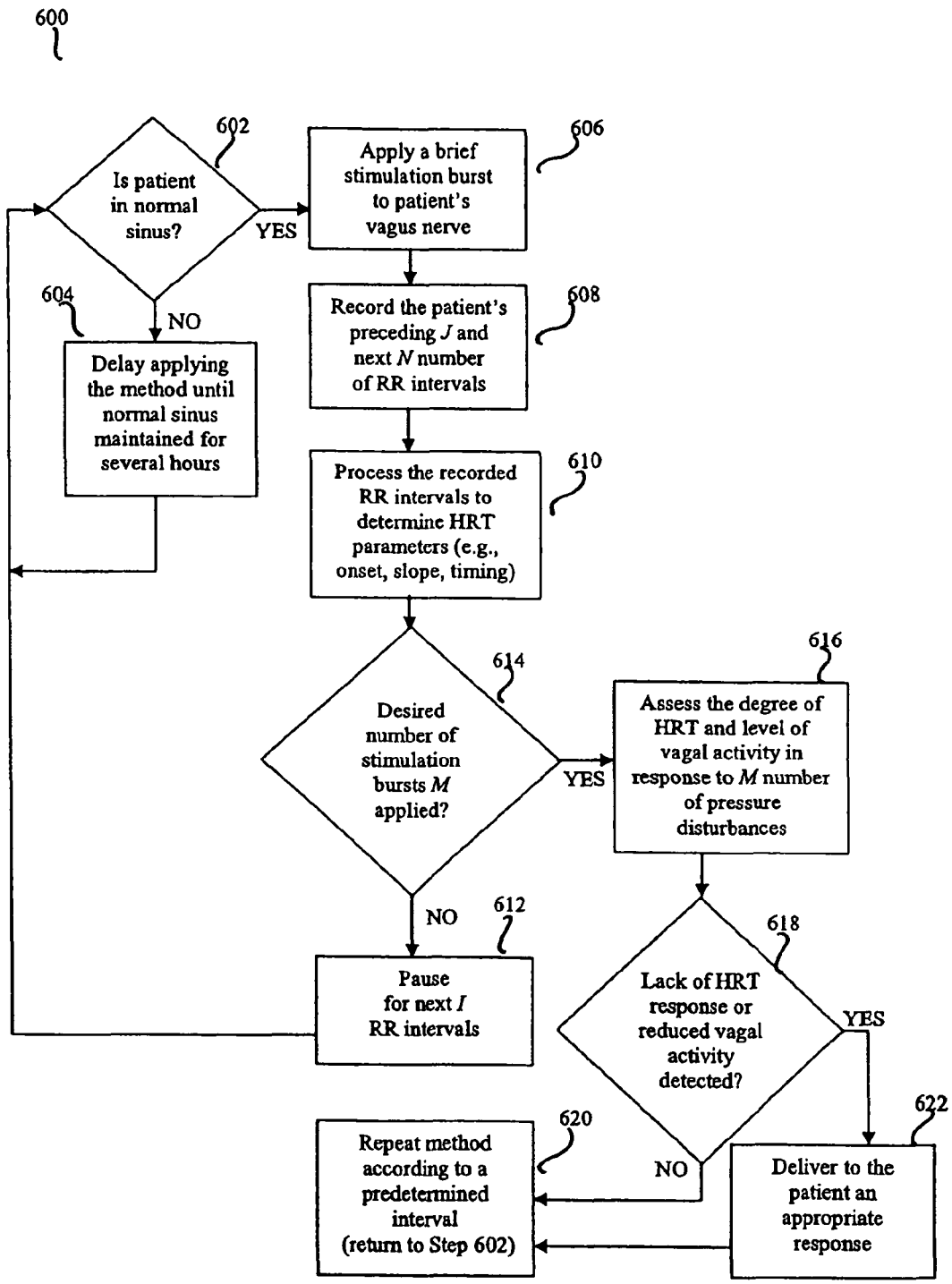
FIG. 6 is a process flowchart, according to an embodiment of the present invention, illustrating a method for using vagal stimulation to measure a degree of HRT in order to assess autonomic tone and a patient's risk of SCD.

FIG. 6 is a process flowchart, according to an embodiment of the present invention, illustrating a method 600 for using vagal stimulation to detect abnormalities in autonomic tone and assess a patient's risk of SCD by measuring HRT absent naturally occurring or artificially induced PVCs. In step 602, it is determined whether the patient has a normal sinus rhythm. If the patient is not in normal sinus (e.g., if arrhythmia is detected) then method 600 is delayed in step 604 until a normal sinus rhythm is restored and maintained for, for example, several hours.

If the patient is in normal sinus, then in step 606, an ICD applies a brief stimulation burst applied via vagal stimulation lead 25, shown in FIG. 1, to the patient's vagus nerve. The vagal stimulation burst will be given through the combined outer two electrodes 31 and 35, and inner electrode 33, which will induce a sudden drop in the patient's arterial blood pressure very similar to that seen immediately following a naturally occurring or artificially induced PVC. The ICD will cease applying stimulation after the first RR interval that is longer than a normal sinus RR interval by at least a factor K, where $1.0 < K < 2.0$ (e.g., K=1.2, K=1.4, etc.). Alternatively, the ICD will cease applying stimulation after a predetermined interval that is longer than one cardiac cycle length during normal sinus but less than two cardiac cycle lengths during normal sinus. Applying a stimulation burst to the patient's vagus nerve for a duration that simulates a compensatory pause will trigger an intrinsic response to a drop in blood pressure without causing an arrhythmia (e.g., the intrinsic response is observed in the form of HRT in low-risk patients, and is not observed at all in high-risk patients).

In step 608, the preceding J number of RR intervals in addition to the next N number of RR intervals are recorded for processing (e.g., the next 20 RR intervals). The invention is not, however, limited to monitoring RR intervals. Based on the description herein, one skilled in the relevant art(s) will understand that the invention can be implemented by monitoring other sinus rhythm intervals. During data collection step 608, ICD back-up pacing must be turned off or at the lowest rate possible in order to avoid pacing during vagal stimulation and a deceleration in heart rate following vagal stimulation.

In step 610, the recorded RR intervals are processed to measure a degree of HRT according to at least one of the following parameters: HRT onset, HRT slope, and HRT timing. The parameters HRT onset, HRT slope, and HRT timing serve as surrogate measures of the level of vagal activity in response to the induced blood pressure disturbance. The invention is not, however, limited to determining these HRT parameters. Based on the description herein, one skilled in the relevant art(s) will understand that the invention can be implemented by measuring other parameters that quantify the oscillatory behavior in RR intervals following a premature event and/or that serve as surrogate measures of the level of vagal activity (e.g., mean magnitude of RR acceleration or deceleration, the overall morphology of the RR oscillation, time course of the overall oscillation, etc.).

In step 614, the number of stimulation bursts applied is compared to a desired number of stimulation bursts M (e.g., M=20 brief bursts of vagal stimulation). If the number of bursts applied does not equal the desired number M, then in step 612, method 600 pauses for I number of RR intervals before applying another stimulation burst. In other words, brief stimulation bursts are applied at a regular interval (e.g., one vagal stimulation burst in every 40 RR intervals).

After the desired number of stimulation bursts are applied, the degree of HRT and level of vagal activity in response to the M pressure disturbances is assessed in step 616. As shown in FIG. 4, the sinus rhythm response of a patient at low risk of SCD contains initial acceleration 414 and late deceleration 416, which are indicative of HRT following a drop in arterial blood pressure. Accordingly, in step 618 of FIG. 6, if the HRT parameters determined in step 610 indicate a lack of HRT in response to the stimulation bursts applied in step 606, then in step 622 an ICD delivers an appropriate response or therapy.

The appropriate therapy can include delivering arrhythmia prevention therapy, including: prolonged vagal stimulation, high voltage shocks, pacing pulses, and drug therapy. In lieu of delivering therapy (e.g., if the device is incapable of delivering these example preventative therapies) or in addition to delivering therapy, method 600 can trigger the ICD to deliver a physician or patient warning, which indicates that the patient is experiencing autonomic abnormalities and is at risk of SCD. The invention is not, however, limited to delivering these example responses. Based on the description herein, one skilled in the relevant art(s) will understand that the invention can be implemented to deliver other preventative therapies in step 622 in response to a lack of HRT or reduced vagal activity. If in step 618 the degree of HRT and level of vagal activity is determined to be normal, then in step 620 method 600 is repeated. Method 600 can be executed at a predetermined interval in order to periodically reevaluate the patient's vagal response.

CONCLUSION

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. A method of assessing a patient's risk of sudden cardiac death (SCD), comprising:

stimulating the patient's vagus nerve to induce a drop in arterial blood pressure; and measuring a degree of oscillatory behavior in sinus rhythm following said stimulation, said degree of oscillatory behavior being indicative of the risk of SCD.

2. The method of claim 1, wherein said stimulating step comprises:
stimulating the patient's vagus nerve with an implantable cardiac device (ICD).

3. The method of claim 2, wherein said stimulating step further comprises:
stimulating the patient's vagus nerve until the occurrence of an R-wave to R-wave (RR) interval having a duration that exceeds a threshold value.

4. The method of claim 3, wherein said threshold value is based on a duration of an RR interval during normal sinus rhythm times a factor K, wherein said factor K is in the range of approximately 1.0 to 2.0.

5. The method of claim 2, wherein said stimulating step further comprises:
stimulating the patient's vagus nerve for a predetermined interval.

6. The method of claim 5, wherein said predetermined interval is greater than a duration of an R-wave to R-wave (RR) interval during normal sinus rhythm, and wherein said predetermined interval is less than two times said duration.

7. The method of claim 2, wherein said ICD aborts the method when said ICD detects an arrhythmia.

8. The method of claim 2, further comprising:
enabling said ICD to deliver therapy to the patient according to the risk of SCD.

9. The method of claim 1, wherein said measuring step comprises:
measuring a degree of heart rate turbulence (HRT).

10. The method of claim 9, further comprising:
indicating that the risk of SCD is relatively high when said measured degree of HRT following said stimulation is relatively low.

11. The method of claim 9, wherein said step of measuring a degree of HRT comprises:
monitoring a first quantity of R-wave to R-wave (RR) intervals preceding and following said stimulation; and
determining at least one HRT parameter for said first quantity of RR intervals.

12. The method of claim 11, wherein said at least one HRT parameter comprises:
HRT onset;
HRT slope; and
HRT timing.

13. The method of claim 11, wherein said step of measuring a degree of HRT further comprises:
pausing for a second quantity of RR intervals after said determining step; and
repeating a desired number of times said stimulating step, said monitoring step, said determining step, and said pausing step.

14. In an implantable cardiac device (ICD), a method of assessing a patient's risk of sudden cardiac death (SCD), comprising:
applying a stimulation burst to the patient's vagus nerve, wherein said stimulation burst induces a drop in the patient's arterial blood pressure;
monitoring a first quantity of R-wave to R-wave (RR) intervals preceding and following said applying step;
measuring a degree of heart rate turbulence (HRT) in said first quantity of RR intervals; and
determining a risk of SCD according to said measured degree of HRT, wherein a relatively low degree of HRT indicates a relatively high risk of SCD.

15. The method of claim 14, wherein said induced drop in arterial blood pressure simulates the patient's cardiovascular response to a premature ventricular contraction (PVC).

16. The method of claim 14, wherein said applying step comprises:
applying a stimulation burst to the patient's vagus nerve until the occurrence of an RR interval having a duration that exceeds a threshold value.

17. The method of claim 16, wherein said threshold value is based on a duration of an RR interval during normal sinus rhythm times a factor K, wherein said factor K is in the range of approximately 1.0 to 2.0.

18. The method of claim 14, wherein said applying step comprises:
applying a stimulation burst to the patient's vagus nerve for a predetermined interval.

19. The method of claim 18, wherein said predetermined interval is greater than a duration of an RR interval during normal sinus rhythm, and wherein said predetermined interval is less than two times said duration.

20. The method of claim 14, wherein the ICD aborts the method when the ICD detects an arrhythmia.

21. The method of claim 14, further comprising:
initiating the method according to a predetermined interval.

22. The method of claim 14, wherein said measuring step comprises:
determining for said first quantity of RR intervals at least one of HRT onset, HRT slope, and HRT timing.

23. The method of claim 14, further comprising:
pausing for a second quantity of RR intervals after said measuring step; and
repeating a desired number of times said applying step, said monitoring step, said measuring step, and said pausing step.

24. The method of claim 14, further comprising:
delivering an appropriate response according to said determined risk.

25. The method of claim 24, wherein said response comprises:
delivering therapy to the patient; and
delivering a warning.

26. The method of claim 25, wherein said therapy is selected from the group consisting of:
delivering prolonged vagal stimulation;
delivering high voltage therapy;
delivering pacing pulses; and
delivering drug therapy.

27. A system for assessing a patient's risk of sudden cardiac death (SCD), comprising:
means for stimulating the patient's vagus nerve to induce a drop in arterial blood pressure;
means for monitoring the patient's sinus rhythm response to said vagal stimulation; and
means for processing said sinus rhythm response to measure a degree of oscillatory behavior, wherein said degree of oscillatory behavior is indicative of the risk of SCD.

28. The system of claim 27, wherein said stimulating means comprises:
an implantable cardiac device (ICD) having at least one lead configured to stimulate the patient's vagus nerve.

29. The system of claim 27, wherein said monitoring means comprises:
means for monitoring a quantity of R-wave to R-wave (RR) intervals preceding and following said stimulation.

30. The system of claim 27, wherein said processing means measures a degree of heart rate turbulence (HRT).

31. The system of claim 30, wherein said processing means measures said degree of HRT by determining at least one of HRT slope, HRT onset, and HRT timing.

32. The system of claim 27, further comprising:
means for delivering appropriate therapy according to the risk of SCD.

33. The system of claim 32, wherein said delivering means comprises:
an implantable cardiac device (ICD) configured to deliver said therapy.

34. An implantable cardiac device (ICD) comprising:
a circuit configured to deliver electric pulses to the vagus nerve to induce a drop in arterial blood pressure;
a sensing circuit to monitor the sinus rhythm response to the induced drop in arterial blood pressure; and
a processor to measure a degree of oscillatory behavior in the sinus rhythm response, wherein the degree of oscillatory behavior is indicative of a risk of sudden cardiac death (SCD).

35. The ICD of claim 34, further comprising:
at least one lead configured to deliver the electrical pulses.

36. The ICD of claim 34, wherein said sensing circuit monitors a quantity of R-wave to R-wave (RR) intervals preceding and following the induced drop in arterial blood pressure.

37. The ICD of claim 34, wherein said processor measures a degree of heart rate turbulence (HRT).

38. The ICD of claim 37, wherein said processor determines at least one of HRT slope, HRT onset, and HRT timing.

39. The ICD of claim 34, further comprising:
a circuit for delivering appropriate therapy according to the risk of SCD.

\* \* \* \* \*